US00RE46696E

(19) United States
(12) Reissued Patent
Kumar

(10) Patent Number: US RE46,696 E
(45) Date of Reissued Patent: Feb. 6, 2018

(54) PROPHY CUP FOR DENTAL HANDPIECE

(71) Applicant: AKHA Limited, Dublin (IE)

(72) Inventor: Ajay Kumar, Irvine, CA (US)

(73) Assignee: AKHA Limited, Dublin (IE)

(21) Appl. No.: 15/191,248

(22) Filed: Jun. 23, 2016

Related U.S. Patent Documents

Reissue of:
(64) Patent No.: 8,784,102
Issued: Jul. 22, 2014
Appl. No.: 13/247,941
Filed: Sep. 28, 2011

U.S. Applications:
(60) Provisional application No. 61/387,467, filed on Sep. 28, 2010.

(51) Int. Cl.
*A61C 3/06* (2006.01)
*A61C 1/12* (2006.01)
*A61C 17/00* (2006.01)
*A61C 1/14* (2006.01)

(52) U.S. Cl.
CPC ..... *A61C 1/12* (2013.01); *A61C 1/141* (2013.01); *A61C 1/145* (2013.01); *A61C 17/005* (2013.01)

(58) Field of Classification Search
CPC ..... A61C 17/005; A61C 17/0202
USPC ..... 433/165, 166, 116, 124–126
See application file for complete search history.

(56) References Cited

U.S. PATENT DOCUMENTS 1,216,311 A 2/1917 Hartman
1,834,726 A 12/1931 Ozon
2,041,077 A 5/1936 Lininger
2,073,137 A 3/1937 Bimrose
2,943,343 A 7/1960 Jankelson
3,579,835 A * 5/1971 Levenson ..... B05C 17/00583 433/82
4,424,036 A 1/1984 Lokken
5,028,233 A * 7/1991 Witherby ..... 433/125
5,131,846 A * 7/1992 Hall ..... 433/116
5,197,876 A * 3/1993 Coston ..... A61C 1/16 433/116
5,209,658 A * 5/1993 Brahler ..... A61C 17/005 433/115
5,348,473 A * 9/1994 Kivlighan, Jr. ..... 433/114
5,380,202 A * 1/1995 Brahler ..... 433/166
5,584,690 A * 12/1996 Maassarani ..... 433/125
5,690,488 A * 11/1997 Spinello ..... A61C 17/005 433/116
5,775,905 A * 7/1998 Weissenfluh et al. ..... 433/166
5,797,744 A * 8/1998 Rosenberg ..... 433/166
6,203,322 B1 * 3/2001 Kraenzle ..... 433/125
(Continued)

*Primary Examiner* — Cary Wehner
(74) *Attorney, Agent, or Firm* — Stetina Brunda Garred & Brucker; Lowell Anderson

(57) ABSTRACT

A prophy cup has an outer surface with dimples formed therein. The dimples increase the turbulent flow in a boundary layer proximate to the surface. The increased turbulent flow reduces the separation of fluid (a slurry of saliva, blood and pumice) at the boundary layer to minimize the quantity of fluid ejected from the surface. A dental handpiece housing is configured to split longitudinally so that a wiper is positioned proximate to the outer surface of the prophy cup. The wiper removes slurry as the prophy cup rotates during a dental cleaning procedure to further reduce the quantity of fluid ejected from the surface during the procedure.

19 Claims, 4 Drawing Sheets

(56) References Cited

U.S. PATENT DOCUMENTS

| | | | | |
|---|---|---|---|---|
| 6,273,716 | B1 * | 8/2001 | Wade | 433/116 |
| 6,948,934 | B2 * | 9/2005 | Wade | 433/116 |
| 7,958,588 | B2 | 6/2011 | Ukaj | |
| 8,566,993 | B1 | 10/2013 | Ukaj | |
| 8,641,417 | B2 | 2/2014 | Kumar et al. | |
| 8,784,102 | B1 | 7/2014 | Kumar | |
| 2006/0292522 | A1 * | 12/2006 | Lees et al. | A61C 17/005 433/116 |

* cited by examiner

Amended

Amended

Amended

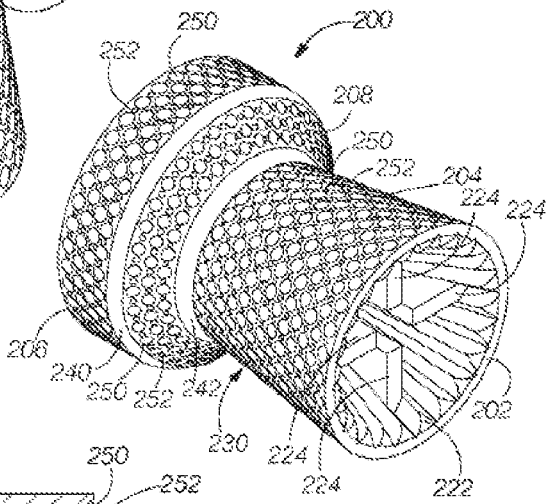
FIG. 5
Amended

PROPHY CUP FOR DENTAL HANDPIECE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

[The present application] *This is a reissue application of U.S. patent application Ser. No. 13/247,941 filed Sep. 28, 2011 and issued Jul. 22, 2015, which* claims [the benefit of] priority [under 35 USC § 119(e)] to U.S. [Provisional Application] *provisional application* No. 61/387,467, filed on Sep. 28, 2010.

BACKGROUND OF THE INVENTION

1. Field of the Invention

The present invention is in the field of prophylactic devices for dental handpieces for remove deposits from surfaces of teeth.

2. Description of the Related Art

One of the most widely used prophylactic devices in the dental profession is known as a prophy cup. A typical conventional prophy cup has a smooth outer surface. The prophy cup is mounted on a dental handpiece. Prophy paste is picked up in the prophy cup and is applied against the tooth surface to remove the deposits. The prophy paste contains abrasive particles and when mixed with saliva it forms slurry. The slurry almost invariably entrains the patient's saliva to form an ever-enlarging rope-like mass which migrates along the surfaces of the cup. The rope-like slurry leaves the cup at its narrowest diameter. The slurry is not confined to the patient's mouth and can be ejected with sufficient velocity to create a contamination area that can be up to 40-50 inches wide and up to 30-40 inches high. The ejected slurry may contain blood-borne pathogens, which can raise the level of contamination.

SUMMARY OF THE INVENTION

Up until now, the phenomena of how the slurry (blood and saliva and pumice from polishing compound) is picked up by the cup and at what point the slurry leaves the cup was unknown. By using CFD (computation fluid dynamics), Applicants have determined that the saliva is picked up at the largest diameter of the cup (the flared portion of the cup that comes in contact with the tooth and the gums) and is released from the cup at its narrowest diameter. Since the outside of the traditional cup has a smooth surface, the saliva has a laminar flow and is more prone to separation. Once separation of a laminar boundary layer occurs, drag rises dramatically because of eddies that form in the gap.

The prophy cup disclosed herein in combination with an improved handpiece reduces the discharge of slurry from a patient's mouth during dental procedures.

One aspect of the disclosed embodiments is a prophy cup having an outer surface with dimples, which may be of varying sizes and shapes. The dimples are configured to increase the turbulent flow in the boundary layer to reduce the separation of the boundary layer. The added dimples minimize the quantity of a slurry of saliva, blood and pumice ejected from the surface of the cup. The dimples retain portions of the slurry as the slurry travels in a spiral from the distal portion of the prophy club to the proximal portion of the prophy cup.

Another aspect of the disclosed embodiments is a housing configured such that the housing is split longitudinally to allow installation of the shafts and gears to rotate the prophy cup. In addition, the housing includes a wiper to remove a slurry of saliva laden with blood and pumice as the prophy cup rotates proximate to the wiper. The wiper can be an integral part of the housing or added to the housing when the shafts and gears are installed.

BRIEF DESCRIPTION OF THE DRAWINGS

Embodiments in accordance with aspects of the present invention are described below in connection with the attached drawings in which:

FIG. 5 illustrates a perspective view of the improved prophy cup of FIG. 4 viewed from bottom;

DETAILED DESCRIPTION OF PREFERRED EMBODIMENTS

Figure 1:
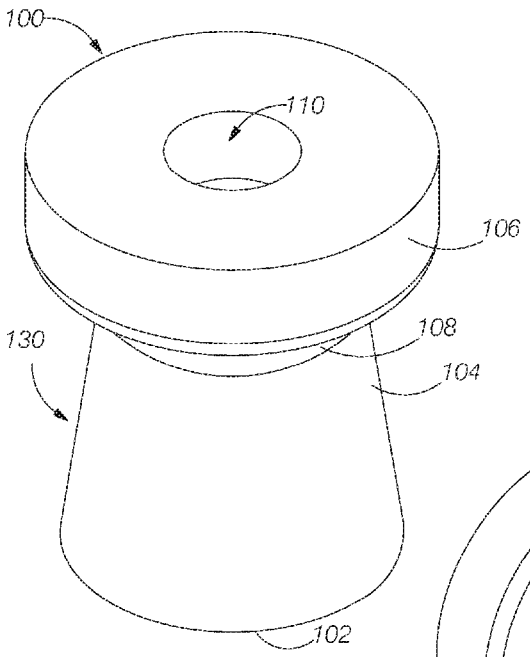
FIG. 1 Prior Art
FIG. 1 illustrates a perspective view of a conventional prophy cup with a smooth outer surface as viewed from the front and top.
Figure 2:
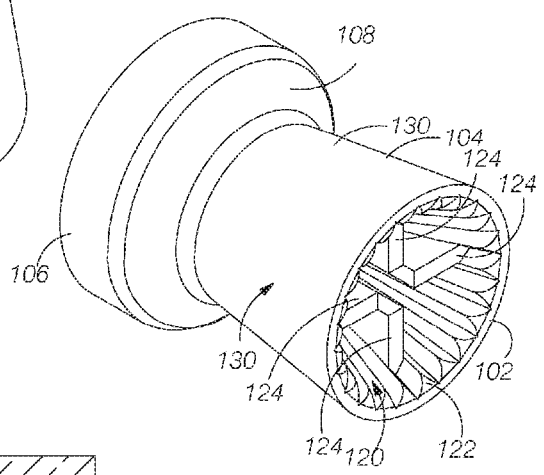
FIG. 2 Prior Art
FIG. 2 illustrates a perspective view of the conventional prophy cup of FIG. 1 as viewed from bottom.
Figure 3:
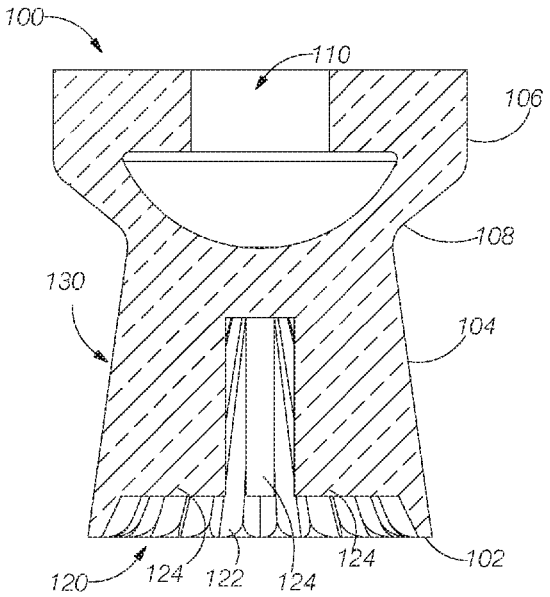
FIG. 3 Prior Art
FIG. 3 illustrates a cross-sectional elevational view of the conventional prophy cup of FIG. 1.

FIGS. 1, 2 and 3 illustrate a typical conventional prophy cup 100 used for polishing the surfaces of teeth during a dental procedure. The prophy cup is generally cylindrical but has a flareable distal portion 102 that transitions to a tapered middle portion 104 that extends from the flareable distal portion to an enlarged proximal portion 106. The diameter of the prophy cup increases rapidly in a transition portion 108 between the tapered middle portion and the enlarged proximal portion. The proximal portion includes an engagement cavity 110 formed in an upper surface 112. The engagement cavity is connectable to a shaft (not shown) of a conventional dental handpiece (not shown). The shaft is rotatable by a conventional power source to cause the prophy cup to rotate at a high angular velocity (e.g., 2,500 RPM) during a dental procedure.

As shown in more detail in the bottom view of FIG. 2 and the cross-sectional view in FIG. 3, the flareable distal portion 102 and the tapered middle portion 104 of the conventional prophy cup 100 have a tapered distal bore 120 formed therein. The tapered distal bore in the illustrated prophy cup has a plurality of flutes 122 formed therein so that when pressure is applied to the prophy cup to force the distal end of the prophy cup against the surface of a tooth, the distal portion flares outward to expose the flutes to the surface of the tooth. In the illustrated prophy cup, the tapered distal bore includes a plurality of ribs 124 that provide internal support to the tapered middle portion for structural stability. Although illustrated with a fluted distal bore with ribs, it should be understood that the distal bore may have other configurations. Dental pumice applied to the distal portion of the prophy cup is transferred to the surfaces of teeth in a patient's mouth when the prophy cup is rotated during a dental procedure.

The conventional prophy cup 100 shown in FIGS. 1, 2 and 3 has a smooth outer surface 130 that extends from the flared distal portion 102 to the enlarged proximal portion 106 via the tapered middle portion 104 and the transition portion 108.

Applicants have discovered that that the pumice mixes with the patient's saliva, and in many cases mixes with the patient's blood, to create a slurry that forms on the surfaces of the flared distal portion 102 of the conventional prophy cup 100. The slurry rapidly migrates in the proximal direction away from the flared distal portion to the tapered middle portion 104 and then to the enlarged proximal portion 106 via the transition portion 108. Applicants have investigated the fluid flow characteristics of the conventional prophy cup and have determined that the smooth outer surface 130 causes the slurry to have a laminar flow, which causes the slurry to be prone to separation from the outer surface of the cup. In addition, the conventional prophy cup has a relatively abrupt diameter change in the transition portion between the tapered middle portion and the enlarged proximal portion, which causes an abrupt increase in surface velocity. The abrupt increase in surface velocity also contributes to the separation of the slurry from the outer surface of the prophy cup.

Figure 4:
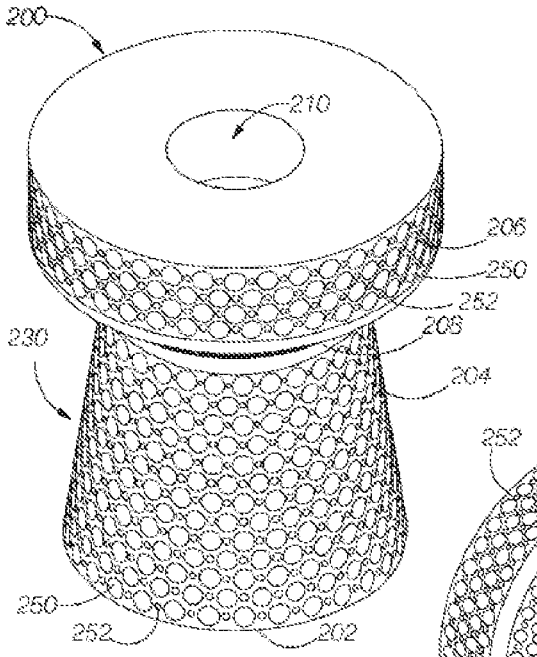
FIG. 4 illustrates a perspective view of an improved prophy cup in accordance with a dimpled outer surface view from the front and top.
Figure 6:
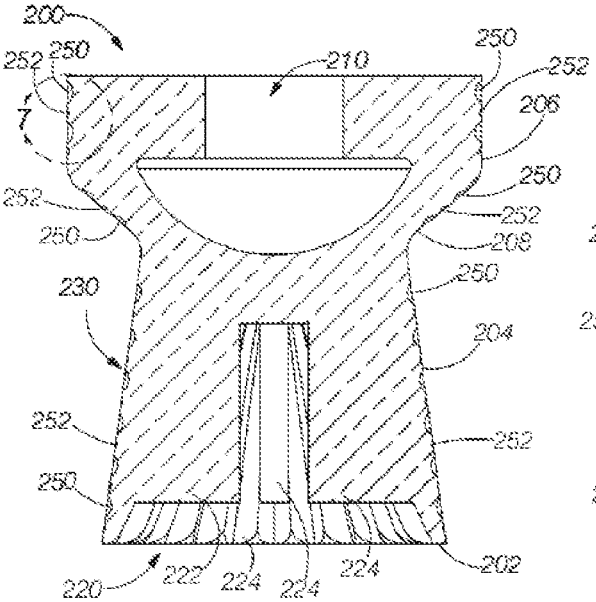
FIG. 6 illustrates a cross-sectional elevational view of the improved prophy cup of FIG. 4.

An improved prophy cup 200 shown in FIGS. 4, 5 and 6 reduces the ejection of the rope-like slurry from the prophy cup during a dental cleaning procedure. The general structure of the improved prophy cup may be similar to the conventional prophy cup 100 of FIGS. 1, 2 and 3 and is illustrated accordingly. In particular, the improved prophy cup of FIGS. 4, 5 and 6 has a flared distal portion 202, a tapered middle portion 204, an enlarged proximal portion 206 and a transition portion 208 between the tapered middle portion and the enlarged proximal portion. The enlarged proximal portion includes a central cavity 210 that is engageable with a dental handpiece that rotates the prophy cup during a dental cleaning procedure. The improved prophy cup of FIGS. 4, 5 and 6 further includes a tapered distal bore 220 with flutes 222 and ribs 224 similar to the flutes and ribs described above.

Unlike the conventional prophy cup 100 described above, the improved prophy cup 200 of FIGS. 4, 5 and 6 has a dimpled outer surface 230. In particular, substantially all of the outer surface of the improved prophy cup from the flareable distal portion 202 to the enlarged proximal portion 206, except for a first undimpled band 240 and a second undimpled band 242, has dimples formed into the surface. The first undimpled band lies between the enlarged proximal portion and the transition portion 208. The second undimpled band lies between the transition portion and the tapered middle portion 204. In alternative embodiments, the entire outer surface may be dimpled.

Figure 7:
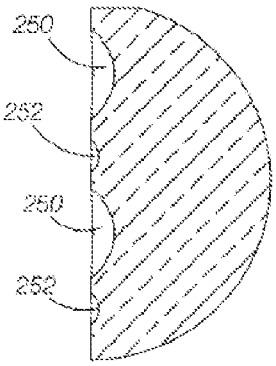
FIG. 7 illustrates an enlarged cross-sectional view taken with the dashed circular area 7 in FIG. 6.

In the illustrated embodiment, the plurality of dimples include a first set of dimples 250 and a second set of dimples 252. As shown in more detail in an enlarged portion of the dimpled outer surface 230 in FIG. 7, the dimples in the first set have larger diameters that the dimples in the second set. For example, in the illustrated embodiment, the dimples in the first set advantageously have diameters at the outer surface of approximately 0.41 millimeter, and the dimples in the second set advantageously have diameters of approximately 0.15 millimeter. The smaller-diameter dimples of the second set are interleaved with the larger-diameter dimples of the first set to provide a larger area of the outer surface that is covered by dimples. In the illustrated embodiment, each dimple extends into the outer surface of the prophy cup to a depth that is less than the spherical radius of the respective dimple. For example, the larger diameter dimples advantageously have a depth of approximately 0.1 millimeter, and the smaller dimples advantageously have a depth of approximately 0.03 millimeters. The diameters and depths of the dimples can be varied.

The dimples 250, 252 on the outer surface 230 of the improved prophy cup 200 introduce turbulent flow in the boundary layer on the outer surface. The turbulent flow reduces the separation of the slurry from the outer surface. The deeper the dimples and more the dimples on the surface, the more the saliva flow becomes turbulent. Even though dimples increase drag slightly when the lifting force experienced by rotating bodies are travelling through a medium, Applicants have determined that the dimples reduce the chances of saliva separation from the outer surface.

The dimples 222, 224 formed into the outer surface 220 of the improved prophy cup 200 introduces turbulent flow to the slurry on the outer surface. Furthermore, portions of the slurry enter the dimples while flowing over the dimples, which minimizes the chances of separation. Although the turbulent flow has more drag initially, turbulent flow provides better adhesion of the slurry to the outer surface, which causes the slurry to be less prone to separation. Turbulent flow also breaks the surface tension, etc. The drag coefficient on the outer surface of the prophy cup increases with dimple depth. The high drag coefficient reduces fluid velocities.

Figure 8:
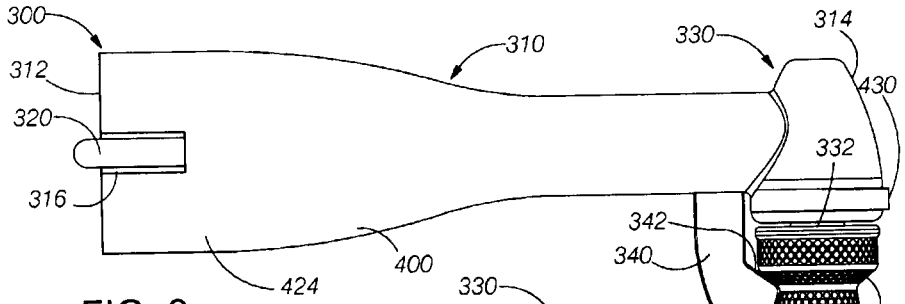
FIG. 8 illustrates a side elevational view of an improved handpiece with the prophy cup of FIGS. 4-7 mounted thereon.
Figure 9:
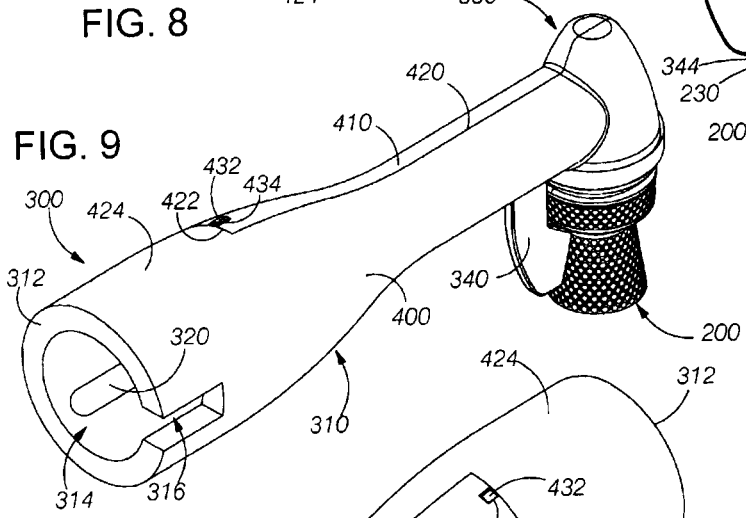
FIG. 9 illustrates a perspective view of the handpiece and prophy cup of FIG. 8 viewed from the proximal end of the handpiece.
Figure 10:
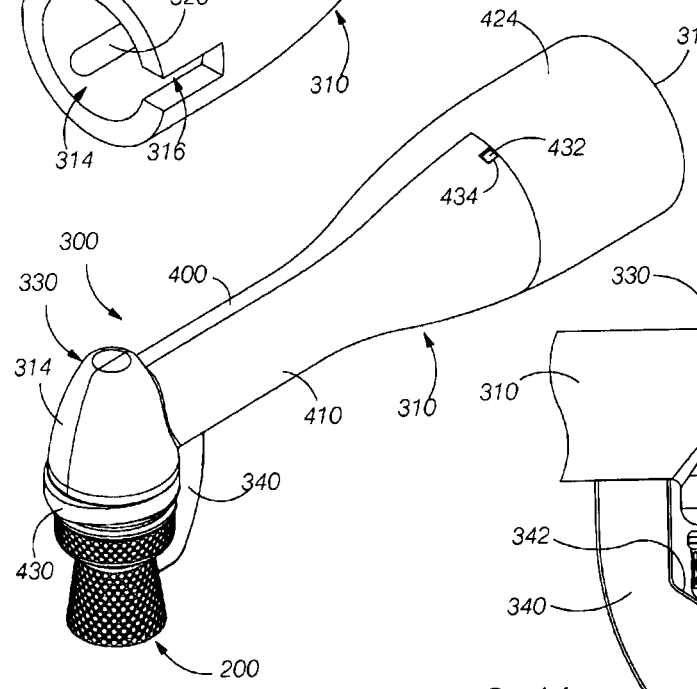
FIG. 10 illustrates a perspective view of the handpiece and prophy cup of FIG. 8 viewed from the distal end of the handpiece.
Figure 11:
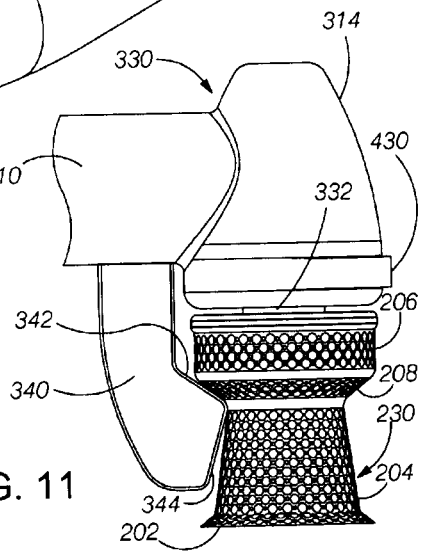
FIG. 11 illustrates an enlarged elevational side view of the proximal end of the handpiece and mounted prophy cup of FIG. 8 further showing the flaring of the flareable distal end of the prophy cup when the distal end of the prophy cup is applied to a surface (not shown)

FIG. 8 illustrates a side elevational view of an improved handpiece 300 with the improved prophy cup 200 of FIGS. 4-7 mounted thereon. FIG. 9 illustrates a perspective view of the handpiece and prophy cup of FIG. 8 viewed from the proximal end of the handpiece. FIG. 10 illustrates a perspective view of the handpiece and prophy cup of FIG. 8 viewed from the distal end of the handpiece. FIG. 11 illustrates an enlarged elevational side view of the proximal end of the handpiece and mounted prophy cup of FIG. 8 further showing the flaring of the flareable distal end 202 of the prophy cup when pressure is applied to the handpiece to force the distal end of the prophy cup against the surface of a tooth (not shown).

The improved dental handpiece 300 of FIGS. 8-11 is useable in combination with the improved prophy cup 200 to further reduce the ejection of slurry from a patient's mouth. The dental handpiece includes a housing 310, which has a proximal end 312 having a cavity 314 that is configured to be mountable to a conventional rotating power source (not shown). A notch 316 in the housing assures that the handpiece is aligned with the power source.

A first shaft 320 is centered within the cavity 314 of the housing 310 to receive the rotational power provided by the power source. The shaft rotates about a first axis (horizontal in FIG. 8) and communicates the rotational power through the housing to a drive head 330 at the distal end of the housing. The drive head includes internal gears (described below) that drives a second shaft 332, which rotates about a second axis (vertical in FIG. 8). The distal end of the second shaft is coupled to the prophy cup 200 to rotate the prophy cup about the second axis. In the illustrated embodiment, the distal end of the second shaft includes a pair of barbs (or teeth) that extend outward from the second shaft. Preferably, the distal end of the second shaft is inserted into the mold when the prophy cup is formed so that the medical-grade silicone material forming the prophy cup flows around the barbs and engages the barbs. Accordingly, the completed prophy cup is securely attached to the second shaft and cannot slip with respect to the shaft when the shaft is rotated.

The improved dental handpiece 300 of FIGS. 8-11 includes a wiper 340, which is positioned below the housing 310 proximal to the drive head 330 and which extends downward proximal to the transition portion 208 and the tapered middle portion 204 of the prophy cup 200. As shown in FIGS. 8 and 11, the wiper includes a first blade edge 342 that is positioned along the outer surface 230 of the prophy cup next to the transition portion of the prophy cup, and includes a second blade edge 344 that is positioned along the outer surface of the prophy cup next to the tapered middle portion of the prophy cup. The clearance between the first and second blade edges of the wiper and the outer surface of the prophy cup is minimized to enable the wiper to remove fluid from the outer surface of the prophy cup as the prophy cup rotates. For example, in certain embodiments, the clearance between the second blade edge and the tapered middle portion of the prophy cup varies from touching (or almost touching) at the proximal (upper in FIGS. 8 and 11) portion of the second blade edge, which is juxtaposed with the undimpled band 242 in FIG. 5, to approximately 0.4 millimeter at the distal lower part of the second blade edge. Similarly, the clearance between the first blade edge and the transition portion of the prophy cup varies from touching (or almost touching) at the distal part of the first blade edge to approximately 0.1 millimeter at the proximal part of the first blade edge. The wiper causes the slurry to be removed from the outer surface of the prophy cup along the smaller outer diameter of the middle portion of the prophy cup before the slurry migrates proximally to the enlarged proximal portion of the prophy cup where the ejection forces are greater. The tighter clearance between the blade edges and the prophy cup near the proximal part of the tapered middle portion of the outer surface assures that substantially all of the slurry is removed prior to reaching the transition portion where the surface velocity increases as the diameter increases. Although the first blade edge and the second blade edge are shown as being relatively blunt in the illustrated embodiment, the wiper can be tapered so that one or both blade edges is thinner and thereby more flexible proximate to the outer surface of the prophy cup. In such embodiments, the blade edges of the wiper can positioned closer to the outer surface of the prophy cup.

The housing 310 of the improved handpiece 300 is preferably formed as a single molded structure similar to a "clam shell" configuration. In particular, as shown in FIGS. 9 and 10, and as shown in more detail in FIGS. 12-17, the housing comprises a main housing portion 400 and a hinged housing portion 410. The two housing portions are joined at a longitudinal seam 420 and a semicircular transverse seam 422. As illustrated the transverse seam is displaced from the proximal end 312 of the housing such that a proximal portion 424 of the housing surrounding the cavity 314 that engages the power source (not shown) is formed as a single molded, generally cylindrical, part that does not have any seams. Accordingly, the dimensions of the cavity in the proximal portion of the housing can be manufactured with close tolerances such that when the handpiece is mounted on the power source, the handpiece is held snugly on the power source and does not move with respect to the power source.

The main housing portion 400 and the hinged housing portion 410 are permanently joined together at a flexible hinge portion 430, which allows the hinged housing portion to rotate from an open position (discussed below) to the closed position shown in FIGS. 9 and 10. In the position, the two housing portions are held together by a pair of tabs 432 (one shown in FIGS. 9 and 10) formed as part of the main housing portion that engage a pair of openings 434 (one shown in FIGS. 9 and 10) formed in the hinged housing portion.

As shown in FIGS. 12-17, the housing 310 in the illustrated embodiment is formed as a single molded structure with the main housing portion 400 and the hinged housing portion 410 interconnected by the flexible hinge portion 430. For example, the two housing portions and the flexible hinge portion are injection molded with a medical-grade plastic material in a conventional manner. As discussed above, the proximal end portion 424 of the main housing portion has the cavity [130] *314* formed therein as part of the injection process. The main housing portion includes the pair of tabs 432, which are spaced apart from the hinge portion by substantially the same distance as the pair of openings 434 formed in the hinged housing portion. The main housing portion also includes a pair of generally oval-shaped protrusions 450, and the hinged housing portion includes a pair of generally oval-shaped recesses 452 that are sized to receive the protrusions. The protrusions are spaced apart from the hinge portion by substantially the same distance as the recesses.

When the hinged housing portion 410 is rotated about the flexible hinge portion 430, the pair of protrusions 450 on the main housing portion are inserted into the pair or recesses 452 in the hinged housing portion to align the hinged housing portion with the main housing portion. In addition, the tabs 432 on the main housing portion enter into and engage with the openings 434 in the hinged housing portion to fixedly secure the two housing portions together. Thus, the tabs and the openings operate as snap joints.

Figure 12:
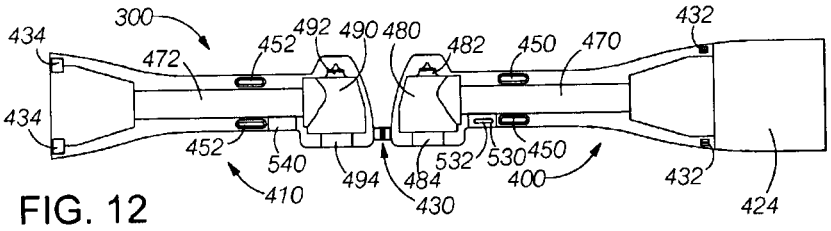
FIG. 12 is an elevational view of the housing of the handpiece showing the main housing portion and the hinged housing portion joined by a hinge portion and showing the features that align and interconnect the two housing portions.
Figure 13:
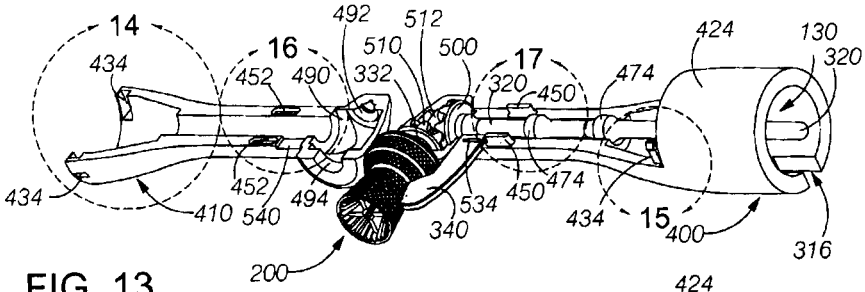
FIG. 13 is a perspective view of the housing of FIG. 13 after installing the shafts, the prophy cup and the wiper and before rotating the hinged housing portion to interconnect the two portion.
Figure 14:
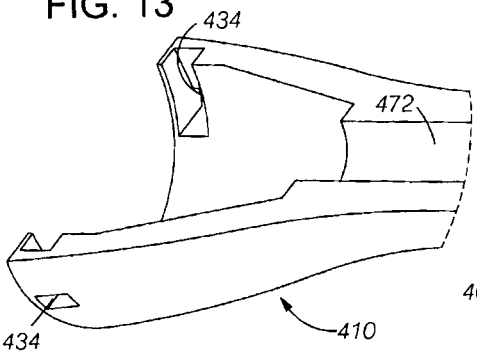
FIG. 14 is an enlarged perspective view of the proximal end of the hinged housing portion taken within the dashed circular area 14 of FIG. 13 to show the openings that receive the tabs to interlock the two housing portions.
Figure 15:
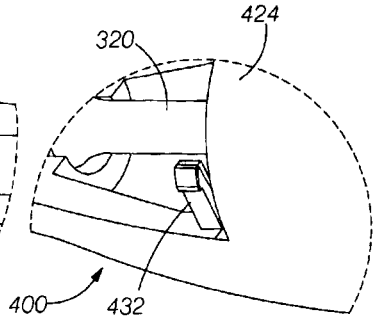
FIG. 15 is an enlarged perspective view of the main housing portion taken within the dashed circular area 15 of FIG. 13 to show the tabs that interlock with the openings in FIG. 14.
Figure 16:
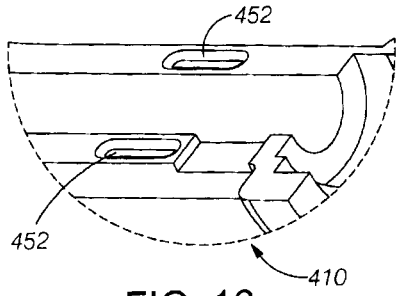
FIG. 16 is an enlarged perspective view of the hinged housing portion taken within the dashed circular area 16 of FIG. 13 to show the alignment recesses.
Figure 17:
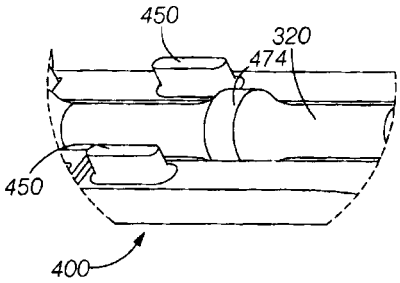
FIG. 17 is an enlarged perspective view of the main housing portion taken within the dashed circular area 17 of FIG. 13 to show the alignment protrusions that engage the alignment recesses of FIG. 16.

As further shown in FIG. 12, the main housing portion 400 includes first half 470 of a first channel that extends to the drive head 330. A corresponding second half 472 of the first channel extends to the drive head in the hinged housing portion 410. When the two housing portions are secured together the two halves of the first channel form a cylindrical channel that supports the first shaft 320. As shown in FIG. 13, the first shaft advantageously includes a pair of enlarged cylindrical portions 474 that act as bearings for the first shaft and that center the first shaft in the cylindrical channel. The first shaft is relatively long with respect to the diameter. By providing the enlarged cylindrical portions at spaced apart locations on the first shaft, the cross section of the first shaft varies along the length of the first shaft. The varying cross section reduces harmonics that might otherwise be produced on the first shaft.

As further shown in FIG. 12, the main housing portion 400 includes an first half 480 of an enlarged cavity in the drive head 330, a first half 482 of an upper bearing chamber and a first half 484 of a lower bearing channel. The hinged housing portion 410 includes a respective second half 490 of the enlarged cavity, a respective second half 492 of the upper bearing chamber and a respective second half 494 of the lower bearing channel.

As shown in FIG. 13, prior to rotating the hinged housing portion 410 and interconnecting the hinged housing portion with the main housing portion 400, the first shaft 320 is positioned in the first half 470 of the first channel. A first bevel gear 500 attached to the first shaft is positioned in the first half 480 of the enlarged cavity in the drive head 330. The second shaft 332 is positioned in the first half 484 of the lower bearing channel. A second bevel gear 510 attached to the second shaft is positioned in the first half of the enlarged cavity with its respective teeth engaged with the respective teeth of the first bevel gear. An extended portion 512 of the second shaft is centered within the first half 482 of the upper bearing channel. When the hinged housing portion is engaged with the main housing portion, the respective second halves of the cavity and the channels are aligned with the respective first halves of the cavity and the channels maintain the proper alignment of the two shafts so that rotation of the first shaft results in rotation of the second shaft via the two bevel gears.

As further shown in FIG. 12, the main housing portion 400 includes a first half 530 of a recessed channel positioned proximal to the drive head 330. An oval-shaped protrusion 532 extends from the first half of the recessed channel. As shown in FIG. 13, the proximal portion of the wiper 340 includes an oval-shaped through-bore 534 that is sized and shaped to receive the third protrusion when the proximal portion of the wiper is positioned in the recessed channel. The proximal portion of the wiper fits snugly within the recessed channel. When the hinged housing portion 410 is engaged with the main housing portion, a second half 540 of the recessed channel in the hinged housing portion also constrains the upper portion of the wiper. The combined effects of the two halves of the recessed channel and the third protrusion prevent the wiper from moving in any direction. Thus, the wiper is properly positioned with respect to the prophy cup 200 as described above.

In an alternative embodiment (not shown), the wiper 340 may be formed as an integral part of either the main housing portion 400 or the hinged housing portion.

In an alternative embodiment (not shown) of the housing 310, the main housing portion 400 and the hinged housing portion 410 are secured together by ultrasonic welding of the medical-grade plastic material. The ultrasonic welding may be used instead of the tabs and openings described above or in addition to the tabs and openings.

In certain embodiments (not shown) of the housing 310, the outer surfaces of the main housing portion 400 and the hinged housing portion may be knurled to enhance a user's ability to grip the handpiece.

As various changes could be made in the above constructions without departing from the scope of the invention, it is intended that all the matter contained in the above description or shown in the accompanying drawings shall be interpreted as illustrative and not in a limiting sense.

What is claimed is:

1. A prophy cup for a dental cleaning system, the prophy cup reducing the ejection of fluids during a dental cleaning procedure, the prophy cup comprising:

a body symmetrical about a rotational axis, the body having an outer surface, the body comprising:

a proximal portion having an interconnection cavity that receives a shaft to rotate the body about the rotational axis;

an intermediate tapered portion that extends distally from the proximal portion; and a flareable distal portion engageable with a dental surface to be cleaned; and a plurality of indented dimples formed on a substantial portion of the outer surface of at least the flareable distal portion and the intermediate tapered portion of the body, the dimples sized and positioned to cause turbulent flow of fluids in a boundary layer proximate to the outer surface of the flareable distal portion and the intermediate tapered portion.

2. A prophy *cup* for a dental cleaning system, the prophy cup reducing the ejection of fluids during a dental cleaning procedure, the prophy cup comprising:

a body symmetrical about a rotational axis, the body having an outer surface, the body comprising:

a proximal portion having an interconnection cavity that receives a shaft to rotate the body about the rotational axis;

an intermediate tapered portion that extends distally from the proximal portion; and a flareable distal portion engageable with a dental surface to be cleaned; and a plurality of dimples formed on a substantial portion of the outer surface of at least the flareable distal portion and the intermediate tapered portion of the body, wherein the plurality of dimples includes at least a first set of dimples having a first size and a second set of dimples having a second size, the dimples having the second size interleaved with the dimples having the first size.

3. The prophy cup as defined in claim 1, wherein each dimple has a respective radius at the outer surface, and wherein each dimple is formed into the outer surface to a respective depth, the respective depth of each dimple being less than the radius of the dimple.

[4. A dental handpiece, comprising:

a first shaft that rotates about a first axis;

a second shaft coupled to the first shaft, the second shaft rotating about a second axis when the first shaft rotates about the first axis;

a prophy cup coupled to the second shaft to rotate about the second axis, the prophy cup having an outer surface, the outer surface having a contour; and a wiper positioned proximal to the prophy cup, the wiper having at least one blade edge, the at least one blade edge having a shape selected to conform to at least a portion of the contour of the outer surface of the prophy cup, the wiper positioned with the at least one blade edge sufficiently close to the outer surface of the prophy cup to remove fluid from the outer surface of the prophy cup and thereby reduce accumulation of fluid on the outer surface.]

5. [The] *A* dental handpiece [as defined in claim 4.], *comprising:*

*a first shaft that rotates about a first axis;*

*a second shaft coupled to the first shaft, the second shaft rotating about a second axis when the first shaft rotates about the first axis;*

*a prophy cup coupled to the second shaft to rotate about the second axis, the prophy cup having an outer surface, the outer surface having a contour; and*

*a wiper positioned proximal to the prophy cup, the wiper having at least one blade edge, the at least one blade edge having a shape selected to conform to at least a portion of the contour of the outer surface of the prophy cup, the wiper positioned with the at least one blade edge sufficiently close to the outer surface of the prophy cup to remove fluid from the outer surface of the prophy cup and thereby reduce accumulation of fluid on the outer surface;* wherein the outer surface of the prophy cup comprises a plurality of dimples formed therein to further reduce the accumulation of fluid on the surface.

6. [The] *A* dental handpiece [as defined in claim 4, wherein:], *comprising:*

*a first shaft that rotates about a first axis;*

*a second shaft coupled to the first shaft, the second shaft rotating about a second axis when the first shaft rotates about the first axis;*

*a prophy cup coupled to the second shaft to rotate about the second axis, the prophy cup having an outer surface, the outer surface having a contour; and*

*a wiper positioned proximal to the prophy cup, the wiper having at least one blade edge, the at least one blade edge having a shape selected to conform to at least a portion of the contour of the outer surface of the prophy cup, the wiper positioned with the at least one blade edge sufficiently close to the outer surface of the prophy cup to remove fluid from the outer surface of the prophy cup and thereby reduce accumulation of fluid on the outer surface;*

*wherein* the first shaft and the second shaft are housed in a housing, the housing comprising a first housing portion and a second housing portion, the first housing portion and the second housing portion interconnectable to form the housing; and the wiper is positioned between the first housing portion and the second housing portion to constrain the wiper at a fixed position proximal to the prophy cup with the at least one blade edge of the wiper adjacent to the outer surface of the prophy cup.

*7. A dental handpiece, comprising:*

*a first shaft that rotates about a first axis;*

*a second shaft coupled to the first shaft, the second shaft rotating about a second axis when the first shaft rotates about the first axis;*

*a prophy cup coupled to the second shaft to rotate about the second axis, the prophy cup having a distal end and an outer surface, the outer surface having a contour; and*

*a wiper positioned proximal to the prophy cup, the wiper having at least one blade edge, the at least one blade edge having a shape selected to conform to at least a portion of the contour of the outer surface of the prophy cup, the wiper positioned with the at least one blade edge sufficiently close to the outer surface of the prophy cup to remove fluid from the outer surface of the prophy cup and thereby reduce accumulation of fluid on the outer surface, the blade edge not extending beyond the distal end of the prophy cup.*

*8. The dental handpiece of claim 7, wherein the wiper is connected to the handpiece.*

*9. The dental handpiece of claim 7, wherein the wiper blade has first and second blade edges to remove fluid from the outer surface of the prophy cup which first and second blade edges are inclined relative to each other at an obtuse angle.*

*10. The dental handpiece of claim 7, wherein the at least one blade is tapered toward the blade edge so as to be more flexible than an outer portion of the at least one blade which is further from the second axis than the tapered blade edge.*

*11. A dental handpiece, comprising: a first shaft that rotates about a first axis:*

*a second shaft coupled to the first shaft, the second shaft rotating about a second axis when the first shaft rotates about the first axis;*

*prophy cup having an outer surface with a distal end, the outer surface having a contour: and*

*a wiper positioned proximal to the prophy cup, the wiper having at least one blade edge, the at least one blade edge having a shape selected to conform to at least a portion of the contour of the outer surface of the prophy cup, the wiper positioned with the at least one blade edge sufficiently close to the outer surface of the prophy cup to remove fluid from the outer surface of the prophy cup and thereby reduce accumulation of fluid on the outer surface, the blade edge extending to a location intermediate a proximal and distal end of the prophy cup.*

*12. The dental handpiece of claim 11, wherein the wiper is connected to the handpiece.*

*13. The dental handpiece of claim 11, wherein the at least one at least one blade edge is straight.*

*14. The dental handpiece of claim 11, wherein the wiper blade has first and second blade edges to remove fluid from the outer surface of the prophy cup which first and second blade edges are inclined relative to each other at an obtuse angle.*

*15. The dental handpiece of claim 11, wherein the at least one blade is tapered toward the blade edge so as to be more flexible than an outer portion of the at least one blade which is further from the second axis than the tapered blade edge.*

*16. A dental handpiece, comprising: a first shaft that rotates about a first axis:*

*a second shaft coupled to the first shaft, the second shaft rotating about a second axis when the first shaft rotates about the first axis;*

*a prophy cup coupled to the second shaft to rotate about the second axis and having an outer surface, the prophy cup having a smaller diameter transition portion and a larger diameter, flarable distal portion having a distal end, the outer surface having a contour: and*

*a wiper positioned proximal to the prophy cup, the wiper having at least one blade edge, the at least one blade edge having a shape selected to conform to at least a portion of the contour of the outer surface of the prophy cup, the wiper positioned with the at least one blade*

*edge sufficiently close to the outer surface of the prophy cup to remove fluid from the outer surface of the prophy cup and thereby reduce accumulation of fluid on the outer surface, the blade edge being inclined relative to the outer surface of the distal end of the prophy cup in an undeformed configuration with a distance between the blade edge being closer to the tapered middle portion of the prophy cup and further away from the distal end of the prophy cup in an undeformed configuration, the blade the having a length along the second axis that is shorter than a length of the prophy cup along the second axis.*

*17. The dental handpiece of claim 16, wherein the wiper is connected to the handpiece and extends in a direction parallel to the second axis.*

*18. The dental handpiece of claim 16, wherein the at least one at least one blade edge is straight.*

*19. The dental handpiece of claim 16, wherein the wiper blade has first and second blade edges to remove fluid from the outer surface of the prophy cup which first and second blade edges are inclined relative to each other at an obtuse angle.*

*20. The dental handpiece of claim 16, wherein the at least one blade is tapered toward the blade edge so as to be more flexible than an outer portion of the at least one blade which is further from the second axis than the tapered blade edge.*

* * * * *